United States Patent
Ma et al.

(10) Patent No.: US 7,794,730 B2
(45) Date of Patent: Sep. 14, 2010

(54) POLYVALENT ATTENUATED LIVE VACCINE FOR PREVENTING AND CURING VIBRIOSIS OF CULTIVATED FISH

(75) Inventors: Yue Ma, Shanghai (CN); Yuanxing Zhang, Shanghai (CN); Dongling Zhao, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 152 days.

(21) Appl. No.: 11/793,170

(22) PCT Filed: Dec. 14, 2005

(86) PCT No.: PCT/CN2005/002187

§ 371 (c)(1),
(2), (4) Date: Oct. 25, 2007

(87) PCT Pub. No.: WO2006/063523

PCT Pub. Date: Jun. 22, 2006

(65) Prior Publication Data

US 2008/0274136 A1    Nov. 6, 2008

(30) Foreign Application Priority Data

Dec. 14, 2004    (CN) .................. 2004 1 0089496

(51) Int. Cl.
*A61K 39/00*    (2006.01)
*C12N 1/20*    (2006.01)

(52) U.S. Cl. .................. 424/200.1; 435/252.1

(58) Field of Classification Search .............. None
See application file for complete search history.

(56) References Cited

U.S. PATENT DOCUMENTS

| | | | |
|---|---|---|---|
| 5,284,653 A | | 2/1994 | Wolf-Watz et al. |
| 5,851,519 A | * | 12/1998 | Dougan et al. ............ 424/93.2 |
| 5,961,983 A | * | 10/1999 | Brey et al. ................ 424/200.1 |
| 6,231,871 B1 | * | 5/2001 | Coloe ........................ 424/258.1 |
| 6,905,691 B1 | * | 6/2005 | Chatfield et al. .......... 424/200.1 |
| 6,913,757 B1 | * | 7/2005 | Nelson ...................... 424/261.1 |
| 2003/0170264 A1 | * | 9/2003 | Turner et al. .............. 424/190.1 |
| 2004/0203039 A1 | * | 10/2004 | Hensel et al. .................. 435/6 |
| 2004/0209367 A1 | * | 10/2004 | Charles et al. ................ 435/471 |
| 2006/0115493 A1 | * | 6/2006 | Hone et al. ................ 424/200.1 |

FOREIGN PATENT DOCUMENTS

| | | |
|---|---|---|
| CN | 1600368 | 3/2005 |
| WO | WO 82/02491 | 8/1982 |
| WO | 03/101482 | * 12/2003 |

OTHER PUBLICATIONS

Liu, Qin et al, Archives of Microbiology, vol. 181, Apr. 2004, pp. 287-293, Cloning, identification and expression of an entE homolgue angE from Vibrio anguillarum serotype 01.*
Wu, H et al, Journal of Applied Microbiology, vol. 97, 2004, p. 1021-1028, Complete sequence of virulence plasmif pEIB1 from the marine fish pathogen Vibrio anguillarum strain MVM425 and location of its replication region.*
Fouz, B et al, Aquaculture, vol. 217, pp. 677-682, 2003, Isolation and new serovar of Vibrio vulnificus pathogenic for eels cultured in freshwater farms.*
Gudding, R et al, Veterinary Immunology and Immunopathology, vol. 72, pp. 203-212, 1999, Recent developments in fish vaccinology.*
Liang, W et al, Infection and Immunity, Oct. 2003, vol. 71(10) p. 5498-5504, Construction and Evaluation of a safe, live oral Vibrio cholerae Vaccine Candidate IEM108.*
Obach, A et al, Vaccination of rainbow trout Oncorhynchus mykiss against the visceral form of coldwater disease, Diseases of Aquatic Organisms, vol. 12, pp. 13-15, 1991, Published Dec. 5.*
Zhu, Yihua et al., "Screening and Iron Supply Optimization of Plasmid pEIB1 Cured Strain of Vibrio anguillarum MVAV6201", *China Academic Journal Electronic Publishing House*, vol. 14, No. 6, May 2004, pp. 64-67, English abstract considered.

* cited by examiner

*Primary Examiner*—Robert B Mondesi
*Assistant Examiner*—Ginny Portner
(74) *Attorney, Agent, or Firm*—Hamre, Schumann, Mueller & Larson, P.C.

(57) ABSTRACT

A novel polyvalent attenuated live bacterial vaccine for preventing and curing vibriosis of cultivated fish is provided. The vaccine mainly comprises attenuated deletion strain of *Vibrio anguillarum* without marker gene, which has significant low toxicity, but remains immunogenicity against wild type strain of *V. anguillarum*, as compared with wild type strain MVM425. Moreover, the vaccine strain has excellent cross immunoprotection against *Vibrio alginolyticus*. The attenuated live vaccine made from the vaccine strain is effective to prevent and cure vibriosis of fish resulted from wild type strain of *V. anguillarum* and *V. alginolyticus*.

12 Claims, No Drawings

POLYVALENT ATTENUATED LIVE VACCINE FOR PREVENTING AND CURING VIBRIOSIS OF CULTIVATED FISH

FIELD OF INVENTION

This invention pertains to techniques for prophylaxis and treatment of aquaculture animals, relating to multivalent (polyvalent) live, attenuated bacterial vaccine for the aquaculture fish. In particular, the invention relates to multivalent live, attenuated vaccine of *Vibiro anguillarum* for prophylaxis and treatment of diseases caused by *Vibiro*, especially *Vibiro anguillarum* and *V. alginolyticus*.

BACKGROUND OF INVENTION

Aquaculture becomes more and more important due to the continuous increase of the world population and the exhaustion of the nature fishery day by day. It is estimated that the production of sea fish product in China should reaches 500,000 tons in 2010 so as to meet the demand for sea fish product. It is difficult to sustainably increase production by increasing culture area due to the limited water and soil resources. Therefore, the tendencies of developing sea fish aquaculture in China are large-scale, intensive and high density. However, with stable development of seawater aquaculture, various diseases increasingly arise, resulting in serious effects on the production and development of the culture. In China, the paroxysmal diseases frequently occur in the fish cultivated in net cage or factory in the recent years. Currently, the rate of losses in the aquaculture in China is more than 30%, amounting to an annual loss of over 16 billion RMB. The diseases have become the primary factors that restrict the healthy development of the aquaculture industry.

The chemical therapy using antibiotic has played an active role for controlling, preventing and curing diseases with respect to occurrence of various diseases. However, the negative influences resulting from this kind of control of diseases, such as environment pollution, significant occurrence of drug-resistant pathogens, residual drug in the aquatic products and the like, become more and more serious. The chemical drugs, such as antibiotics as the primary drugs, have been gradually forbidden in the culture fishery in EU, US and CA. According to the stipulations in the White Book of Food Safety in EU, the cultivated aquatic products using antibiotic drugs are forbidden to enter into the trading market in the states of EU. Many antibiotic drugs are also forbidden to use in Japan in the prophylaxis and treatment of diseases in cultivated fish and shrimps.

As a major country in the field of culture fishery in the world, the export of seafood in China only comprises about 6% of the total amount of cultivated products. One of the major confinement factors is that there is serious safety problem in the Chinese aquatic products. The residual amounts of drugs and deleterious agents are seriously above the standard. This is the major obstacle that restricts the expansion of the export. In recent years, the export of aquatic products of China is restricted by EU, Japan and many other nations and regions due to the safety problem. Meanwhile, because the diseases are serious and paroxysmal, in order to reduce the risk of suffering from diseases, the producers generally harvest the product ahead of time, resulting in that product tends to be small. This also affects the rate of export and the export price. To enhance the international market competition of the culture fishery and to enlarge the export of the aquatic products, China has advanced, established and extended the technical standard on nuisance free cultivation, wherein one of the major technical indexes is the prohibition of use of antibiotic drugs, thereby ensuring the safety of aquatic products.

To inhibit the development trend of gradually serious diseases in cultivated fish resultant from various environment factors and the sharp increase of the culture density and the like as well as to improve the sustainable development of the marine culture fishery, the State of World and Agriculture has proposed a so-called System Management Approaches (SMA) culture mode to prevent occurrence of various diseases according to the successful experiences in the fishery development in the developed countries (Ormonde P. Fisheries resources: trends in production, utilization and trade. In: Nomura I (ed.). The State of World Fishery and Agriculture 2002. Rome: FAO Information Division, 2002, p 3-45). One of the major means in this approach is the proposal of use of various vaccination techniques for prophylaxis and treatment represented by vaccine vaccination. Use of these measures will greatly reduce the use of chemical drugs. This will eliminate the environment pollution and improve consume safety of the aquatic products. As an economic and effective disease-controlling policy and means which is in accordance with the environment-friendly and sustainable development strategy, vaccination becomes the major leading and application field in the study and development of the modern aquaculture standard in various countries of the world.

Vaccine exhibits properties of strong pertinence, long period of against disease, absolute immunity, significant effects and positive prophylaxis and treatment. The kill vaccine, which is present in an inactivated form of pathogenic bacteria cell as the basis form, provides effective means for prophylaxis and treatment of diseases of aquaculture. However, the kill vaccine has a common technical application deficiency that its administration is inconvenient. Only by injection administering, can it provide relatively good immunoprotection. This is greatly inconvenient for the fish culture in which thousands of fish need to be vaccinated. The cost of administration is generally not acceptable in the culture fishery. Moreover, it is impossible to administer the fish fry and young fish which are seriously diseased by injection of drugs. Furthermore, the effect of the kill vaccine generally is ineffective or is not good enough to treat many diseases. All of these deficiencies impede the wide use of the prophylaxis and treatment techniques by vaccination in the aquaculture.

According to the industry feature of the culture fishery, it is required that the techniques for the prophylaxis and treatment of diseases should be economic and convenient for operation. Therefore, in addition to the technical requirement of high valence, the development of the vaccine product should have low cost which cannot exceed the capacity for acceptance in the culture industry. The attenuated live vaccine has become the focus and leading field in the current study and development of the aquaculture vaccine in the world due to its new technical advantages, such as convenient administration (it may be administered by immersion), high titer of vaccination (the administration dose may be reduced), low cost, and possibility of developing broad spectrum vaccine (Generally, the live bacterial vaccine possesses cross protection).

Bacteria belonging to the genus *Vibrio* are the most common pathogens responsible for bacterial diseases in marine culture fishes, such as vibriosis. These bacteria occur at a wide range of temperature, last a long period and cover a wide range of zones. They endanger many kinds of fishes, for example most of the marine fishes such as Percidae, Mugilidae, Bothidae and Pleuronectidae. The pathogens that currently cause relatively serious vibriosis in the cultivated fishes in China mainly include *Vibiro anguillarum, Vibiro alginolyticus* and *Vibrio parahaemolyticus*. *Vibiro anguillarum* mainly and seriously endangers the rare economic fishes, e.g., Bothidae (such as *Paralichthys olivaceus* and *Scophthalmus maximus*), Sparidae (such as *Pagrosomus major*) and *Lateolabrax japonicus* and the like in the aquaculture fished in northern China, while *Vibiro alginolyticus* is the main vibriosis pathogen in the primary cultivated economic fishes (such as *Epinephelus coioids*, and *Pseudosciaena crocea* etc.) in southern China. These vibriosises are highly dangerous and infectious. There are no effective means for prophylaxis and treatment in China.

*Vibrio anguillarum* mainly causes hemorrhaging sapraemia in the cultivated fish. The main pathogenic virulence factor of *Vibrio anguillarum* is the pJM1 like plasmid-encoding iron uptake system in *Vibrio anguillarum* (Wu H., Ma Y., et al. Complete sequences of virulence plasmid pEIB1 from the marine fish pathogen *Vibrio anguillarum* strain MVM425 and location of its replication region. Journal of Applied Microbiology, 2004, 97:11021-1028). The inactivated vaccines used for prophylaxis and treatment of vibriosis caused by *Vibrio anguillarum* have been successfully developed and commercialized. Since the cultivated fish are generally infected by several Vibrio pathogens, the inactivated vaccines available abroad are mainly combined vaccines produced from several vibriosis pathogens. Currently, there are not any types of commercialized vaccines for vibriosis in China which are mainly directed to the prophylaxis and treatment of diseases caused by *Vibrio anguillarum*. It is reported in U.S. Pat. No. 5,284,653 the utilization of transposon insertion technique for mutation to construct attenuated live *Vibrio anguillarum* vaccine. There are not any other types of developing attenuated live *Vibrio anguillarum* vaccine reported in the literature at home and abroad.

The attenuated live vaccine developed by using gene recombination and construction techniques such as transposon and the like contains antibiotic resistant genes and exogenous gene fragments, which may be transferred into the other pathogens. Therefore, they exhibit congenital potential risk of endangering environment. The reversion of virulence and the risk of uncontrollable environment transmission of this kind of vaccines should be taken care and solved when using. In view of these risks, this kind of attenuated vaccine is regarded as biological preparation having relatively high risk of environment safety under the law and regulation on examination and approval executed by the Inspect and Management Institution for Biological Preparation in various countries, including China. Thus, it is difficult to enter into the commercial development procedure.

The technique for constructing the attenuated deletion vaccine without marker gene (or vaccine with unmarked gene deletion) is the newly developing field for development of live vaccine in the world, which is an international leading field and a main development aspect for development of vaccine. The vaccine thus developed exhibits reliable product and environment safety. Moreover, the constructed attenuated strains exhibit potential value of expressing exogenous antigen and developing polyvalent vaccine, especially against diseases caused by virus. Therefore, it becomes an international leading field and a main development aspect for development of vaccine.

The attenuated live vaccine constructed by this technique exhibits the following advantages as compared with those constructed by the traditional techniques:

a) The attenuated live vaccine thus developed does not contain any antibiotic resistant gene. Therefore, it does not exhibit the potential harm resulted from transmission of antibiotic resistance.

b) By using the technique of gene deletion mutation, especially double deletion, it is believed that the virulence cannot revert. As a result, the possibility of transferring a great amount of toxic pathogens to the environment can be greatly eliminated.

c) The genetic background of the mutation is clear, and the attenuation principle is definite. Therefore, it is easy to distinguish the vaccine strain from the wild type strain. As a result, it is convenient to monitor the environment and to improve the environment safety and controllability of vaccine.

All of these technical safety features provide feasible development and application prospect for the commercialized procedure of the attenuated deletion live vaccine without marker gene.

SUMMARY OF INVENTION

An object of the invention is to provide a novel polyvalent live, attenuated bacterial vaccine, which can eliminate the potential for risking environment and product safety commonly present in the traditional attenuated live vaccine, thereby compensating the technical application deficiencies of monovalance of the live vaccine and the inconvenient administration so as to provide a polyvalent, safe and economic vaccine for prophylaxis and treatment of diseases of cultivated fish caused by *Vibrio*.

To achieve the above object, in the first aspect, the invention is to provide a polyvalent live, attenuated bacterial vaccine comprising an attenuated deletion mutant strain of *Vibiro* without marker gene or mutant strain of *Vibiro* with unmarked gene deletion, wherein the synthesis of the aromatic amino acids, folic acid and/or the virulence factor, siderophore anguibactin, of the attenuated deletion mutant strain of *Vibiro* without marker gene is repressed or deficiency as compared with the wild type strain.

In a preferred embodiment, said *Vibrio* includes, but is not limited to, *V. anguillarum*, *V. alginoylticus*, *V. parahaemolyticus* and *V. harveyi*. In another embodiment, the *Vibrio* is the *V. anguillarum* strain MVM425.

In still another embodiment, the polyvalent live, attenuated bacterial vaccine comprises *V. anguillarum* deletion strain MVAV6203 without marker gene (CCTCC accession number M204066), *V. anguillarum* deletion strain MVAV6204 without marker gene (CCTCC accession number M204067), and/or *V. anguillarum* deletion strain MVAV6201 with endogenous toxic plasmid deleted (CCTCC accession number M203069).

In another embodiment, the aro C gene and/or angE gene and/or the endogenous plasmid pEIB1 is/are deleted in said attenuated deletion mutant strain without marker gene.

In an embodiment, the concentration of the attenuated deletion mutant strain without marker gene is $10^6$-$10^9$ CFU/ml.

In another embodiment, said vaccine further comprises marine saline. In a preferred embodiment, the marine saline comprises NaCl, 20 g/l; KCl, 0.7 g/l; $MgCl_2 \cdot 6H_2O$, 4.8 g/l; $NaHCO_3$, 0.11 g/l; $MgSO_4 \cdot 7H_2O$, 3.5 g/l; and $CaCl_2 \cdot 2H_2O$, 1.6 g/l; pH 7.2.

In the second aspect, the invention is to provide a method for prophylaxis and treatment of vibriosis of the cultivated fish, comprising injecting or immersing said cultivated fish with the polyvalent live, attenuated vaccine as claimed in claim 1.

In an embodiment, said cultivated fish includes, but is not limited to Percidae, Mugilidae, Balistidae, Bothidae, Pleuronectidae, Bothidaes, and Sparidae. In a preferred embodiment, the cultivated fish includes, but is not limited to *Paralichthys olivaceus, Scophthalmus maximus, Pagrosomus major, Lateolabrax japonicus, Epinephelus coioids,* and *Pseudosciaena crocea.*

In an embodiment, the way of administration includes, but is not limited to, injection and immersion. In an embodiment, when administering by injection, the concentration of injection is $10^4$-$10^8$ CFU/fish; when administering by immersion, the concentration of immersion administration is $10^4$-$10^8$/ml and the administration time is 1-15 minutes.

In an embodiment, the vibrio includes but is not limited to *V. anguillarum, V. alginoylticus, V. parahaemolyticus* and *V. harveyi.*

In an embodiment, the polyvalent live, attenuated bacterial vaccine comprises *V. anguillarum* deletion strain MVAV6203 without marker gene (CCTCC accession number M204066), *V. anguillarum* deletion strain MVAV6204 without marker gene (CCTCC accession number M204067), and/or *V. anguillarum* deletion strain MVAV6201 with endogenous toxic plasmid deleted (CCTCC accession number M203069).

In the third aspect, the invention relates to use of the polyvalent attenuated, live vaccine in the preparation of a medicament for prophylaxis and treatment of vibriosis of cultivated fish.

In an embodiment, the polyvalent live, attenuated bacterial vaccine comprises *V. anguillarum* deletion strain MVAV6203 without marker gene (CCTCC accession number M204066), *V. anguillarum* deletion strain MVAV6204 without marker gene (CCTCC accession number M204067), and/or *V. anguillarum* deletion strain MVAV6201 with endogenous toxic plasmid deleted (CCTCC accession number M203069).

In the preferred embodiments, the attenuated mutant strain of the invention does not carry any antibiotic resistant markers or any other markers or any exogenous gene fragments.

DETAILED DESCRIPTION OF INVENTION

The wild type *Vibrio angullarum* strain MVM425 used in the invention was isolated from the diseased fish suffered from vibriosis epizootic in the fishery in the Yellow Sea of China (*Vibrio angullarum* strain MVM425, Ma Yue et al., "preparation of vaccine directed to the vibriosis of cultured fish optimization of a novel simple culture for *Vibrio angullarum*", *High Technology Letters*, Vol. 11(7), 2001). This wild type strain contains in the chromosome the synthesis gene for aromatic amino acid metabolism routine, aroC (Q. Chen, et al. Chromosome-mediated 2,3-Dihydroxybenzoic acid is a prescursor in the biosynthesis of the plasmid-mediated siderophore anguibactin in *Vibrio anguillarum*. *J. Bacteriol.* 1994, 176:4226-4234), deletion of which will result in aromatic amino acid auxotrophic mutants. It was confirmed that this strain further carried pEIb1 plasmid and the complete sequences of pEIB1 has been determined (GenBank accession no. AY255699). This plasmid is an pJM1-like wild endogenous free plasmid, which encodes an iron uptake system. Deletion of this plasmid will result in iron auxotrophic mutants. The angE gene is an important gene in the synthesis of the iron uptake system of *Vibrio anguillarum* encoded by pEIB1, deletion of which will result in iron auxotrophic mutants (Qin L. Ma Y. et al. Cloning, identification and expression of an entE homologue angE from *Vibiro anguillarum* serotype O1. *Arch Microbiol,* 2004, 181:287-293).

Deletion of the above target genes will prevent the synthesis of aromatic amino acid, folic acid and virulence factor, siderophore anguibactin, in the wild type strain of *Vibrio angullarum*, so that the virulence the wild type strain of *Vibrio angullarum* and its ability of colonization in nature environment and fish body are greatly reduced. As a result, the attenuation can be realized.

The term "repress", "repressed" or "repression" used herein means the synthesis of aromatic amino acid, folic acid and/or the virulence factor, siderophore anguibactin, of the attenuated deletion mutant strain without marker gene is reduced or even completely eliminated as compared with the wild type strain.

In the method of the invention, the culture medium used for attenuated vaccine strain may be the LB medium, supplemented with NaCl (2.5%) and the following amino acids (20 mg/L): phenylalanine, tyrosine, tryptophane, p-amino benzoic acid, p-hydroxy benzoic acid. The peptone can be selected from the group consisting of casein peptone, tryptone peptone or soybean protein peptone. Soybean protein peptone is preferably used in the invention. The medium must contain 0.2-0.5 mM of $Fe^{3+}$. Said $Fe^{3+}$ may be present in a form of such as ferric citrate or $FeCl_3$. Preferably, ferric ammonium citrate is used in the invention.

In the invention, three deletion mutant strains without marker gene are derived from wild type strain MVM425, and are designated as MVAV6201 (pELB1 plasmid is completely deleted), MVAV6203($\Delta$aroC), and MVAV6204 ($\Delta$aroC$\Delta$angE), respectively. They have relatively low virulence as compared with the wild type strain MVM425 and can effectively protect the test fish from damage caused by the strongly pathogenic vibrio strains, wild type strain of *Vibrio angullarum* and *V. alginoylticus*. MVAV6201 was deposited in China Center for Type Culture Collection (CCTCC, Wuhan University of China, 430072) on Sep. 19, 2003 with accession number CCTCC-M203069. MVAV6203 and MVAV6204 were deposited in CCTCC on Sep. 7, 2004 with accession numbers CCTCC-M204066 and CCTCC-M204067, respectively.

The immune effects of the live vaccine of the invention are significant as evidenced by the experiments disclosed below. The live vaccine of the invention has very good prophylaxis and treatment effect on the vibriosis of the aquaculture fish. Meanwhile, it can provide cross immunoprotection for the test fish against *Vibrio angullarum* and *V. alginolyticus*, indicating a significant polyvalent immune protection. In particular, the vaccine can be conveniently administered by immersion for immunization to produce highly effective immune protection. Meanwhile, all of the attenuated vaccine strains do not contain any exogenous gene fragments or antibiotic-resistant marker genes and the majority of their virulence genes and virulence-related genes were deleted, resulting in that the virulence cannot be recovered. Therefore, technically, the vaccine is environment friendly and safe to product and possesses commercial development and application value.

Generally, marine saline is used to formulate the vaccine of the invention. The other excipients, carriers, adjuvants known to the skilled in the art can also be used to formulate the vaccine. The marine saline generally contains NaCl 10-30 g/L, KCl 0.5-1.0 g/L, $MgCl_2.6H_2O$ 3-6 g/L, $NaHCO_3$ 0.05-

0.15 g/L, $MgSO_4.7H_2O$ 2-6 g/L, and $CaCl_2.2H_2O$ 1-2 g/L, pH7.0-7.8. The preferred marine saline may contain NaCl 20 g/L, KCl 0.7 g/L, $MgCl_2.6H_2O$ 4.8 g/L, $NaHCO_3$ 0.11 g/L, $MgSO_4.7H_2O$ 3.5 g/L, $CaCl_2.2H_2O$ 1.6 g/L, pH7.2. In another embodiment of the invention, the vaccine of the subject application may be formulated into a freeze-dried formulation.

In the invention, preferably, *V. anguillarum* deletion strain MVAV6203 without marker gene, *V. anguillarum* deletion strain MVAV6204 without marker gene, and/or *V. anguillarum* strain MVAV6201 with endogenous toxic plasmid deleted can be used alone or in combination. Further, the vaccine may contain any other vaccine strains to formulate a combined vaccine.

The invention will be set forth below with specific examples. It should be understood that the invention is not limited to these specific examples, which are just illustrative. The scope of the invention should be defined by the contents in the claims.

EXAMPLE 1

Preparation of Attenuated Live Vaccine

Compositions of medium and marine saline:

1) LB medium: soybean protein peptone (Difco) 10 g/L; yeast extract (Merck), 5 g/L; NaCl, 25 g/L; agar 18 g/L, pH7.5.

2) Seedling medium: soybean protein peptone (Difco) 110 g/L; yeast extract (Merck), 5 g/L; NaCl, 25 g/L; phenylalanine 20 mg/L; tyrosine 20 mg/L; tryptophan 20 mg/L; p-hydroxy benzoic acid 20 mg/L; p-hydroxy benzoic acid 20 mg/L; pH7.5.

3) Fermentation medium: soybean protein peptone (Difco) 110 g/L; yeast extract (Merck), 5 g/L; NaCl, 25 g/L; ferric ammonium citrate, 0.2-0.5 mmol; phenylalanine 20 mg/L; tyrosine 20 mg/L; tryptophan 20 mg/L; p-hydroxy benzoic acid 20 mg/L; p-amino benzoic acid 20 mg/L; pH6.8.

4) Marine saline: NaCl 20 g/L, KCl 0.7 g/L, $MgCl_2.6H_2O$ 4.8 g/L, $NaHCO_3$ 0.11 g/L, $MgSO_4.7H_2O$ 3.5 g/L, $CaCl_2.2H_2O$ 1.6 g/L, pH7.2. Sterilized by filtering.

Preparation of Vaccine: One inoculating loop of seeds of the attenuated vaccine strains were obtained from the LB slant culture on which said seeds were stored. The seeds were inoculated into 100 ml of liquid LB seedling medium contained in the 500 ml flask. The flask was agitated for culture at 28° C. (200 rounds per minute, rpm). Twelve hours later, 5 ml of the culture with heavy growth (O.D. was about 4.0) were inoculated into 100 ml of fresh fermentation medium. Then, cultivation was carried out at 28° C. for 12 hours. The cultures were washed with sterilized marine saline three times. The cells were harvested by centrifugation (2000 g, 15 min, 15° C.). Then, the cells were diluted with sterilized marine saline, thereby forming a suspension with a concentration ($10^6$-$10^9$CFU/ml) which was stored at 15° C. until use.

EXAMPLE 2

50% Lethal Dose ($LD_{50}$) Determined by Using *Paralichthys olivaceus* as Test Animal Test fish were maintained in the specific pathogen free (SPF) laboratory for acclimating for 1 week to remove the abnormal individuals. Before infection, the fish in SPF laboratory were cultured in the 20 L of tank for infection assay in the Challenge Lab continuously for 1 week (20 fish/tank). The average length was 12-15 cm per fish. Two of third of the culture water in the experimental tanks were replaced daily with the sterilized seawater. The temperature of the water was 20° C.±2° C.

The test fish were grouped randomly. Two tanks were used in each group for parallel experiment. In the infection experiment, the test fish in each group were artificially infected via intramuscular injection with a certain concentration gradient doses ($10^2$-$10^8$ CFU/fish) of *Vibrio angullarum* wild type strain and attenuated vaccine strains. The number of the dead fish in each group under each infection dose within 10 days were recorded. The mortality was calculated to determine $LD_{50}$ (Table 1).

TABLE 1

Pathogenicity of *V. anguillarum* toxic strain MVM425 and attenuated strains on *Paralichthys olivaceus*

| Strain | Treatment dose | Number of dead fish | Number of test fish | Mortality (%) |
|---|---|---|---|---|
| MVM425 | $1 \times 10^3$ CFU/fish | 10 | 20 | 50 |
| MVAV6201 | $1 \times 10^8$ CFU/fish) | 0 | 20 | 0 |
| MVAV6203 | $1 \times 10^8$ CFU/fish | 0 | 20 | 0 |
| MVAV6204 | $1 \times 10^8$ CFU/fish | 0 | 20 | 0 |
| Control | 0.85% saline, 0.2 ml/fish | 0 | 20 | 0 |

Note:
The above data were the average obtained from two groups of independent parallel experiments.

The results indicated that all of the attenuated strains possessed significant attenuation effect as compared with *Vibrio angullarum* wild type strain. The attenuated strains were basically not toxic in the range of test concentration to Paralichthys olivaceus.

EXAMPLE 3

50% Lethal Dose ($LD_{50}$) Determined by Using *Epinephelus coioids* as Test Animal Test fish were maintained in the specific pathogen free (SPF) laboratory for acclimating for 1 week to remove the abnormal individuals. Before infection, the fish in SPF laboratory were cultured in the 20 L of tank for infection assay in the Challenge Lab continuously for 1 week (10 fish/tank). The average length was 12-15 cm per fish. The water in the tank were maintained flow (300-400 ml/min, sterilized aged seawater). The temperature of the water was 28° C.±2° C.

The test fish were grouped randomly. Three tanks were used in each group for parallel experiment. In the infection experiment, the test fish in each group were artificially infected via muscle injection with a certain concentration gradient doses ($10^2$-$10^8$CFU/fish) of *V. alginolyticus* wild type strain and attenuated vaccine strains. The number of the dead fish in each group under each infection dose within 10 days were recorded. The mortality was calculated to determine $LD_{50}$ (Table 2).

TABLE 2

Virulence of *V. alginolyticus* wild type strain and attenuated vaccine strains in *Epinephelus coioids*

| Strain | Treatment dose | Number of dead fish | Number of test fish | Mortality (%) |
|---|---|---|---|---|
| MVM425 | $1 \times 10^5$ (CFU/fish) | 16 | 30 | 53.3 |
| MVAV6201 | $1 \times 10^8$ (CFU/fish) | 0 | 30 | 0 |
| MVAV6203 | $1 \times 10^8$ (CFU/fish) | 0 | 30 | 0 |
| MVAV6204 | $1 \times 10^8$ (CFU/fish) | 0 | 30 | 0 |
| Control | 0.85% saline, 0.2 ml/fish | 0 | 30 | 0 |

Note:
The above data were the average obtained from two batches of independent parallel experiments.

The results indicated that all of the attenuated strains possessed significant attenuation effect as compared with *V. alginolyticus* wild type strain. The attenuated strains were basically not toxic in the range of test concentration to *Epinephelus coioids*.

EXAMPLE 4

Immunoprotection Assay by Injection, Using *Paralichthys olivaceus* as Test Animal The test fish of *Paralichthys olivaceus* were grouped randomly into 12 groups. Each group had three parallel tanks, 10 fish/tank. The fish were vaccinated with the prepared attenuated live vaccines by intramuscular injection. The test fish of *Paralichthys olivaceus* were intramuscularly injected with vaccination doses of $10^6$CFU/fish and $10^8$CFU/fish. The control group was injected with sterilize saline. 4 weeks after vaccination, the vaccinated Paralichthys olivaceus of each group were artificially challenged by intramuscularly injecting $10^8$ CFU of the wild-type *V. anguillarum* strain per fish. The number of the dead fish were observed and counted within 15 days to calculate the ratio of immunoprotection (see Table 3).

The ratio of immunoprotection was calculated based on the following formula:

% Immunoprotection=(mortality of the control group−mortality of the vaccination group)/(mortality of the control group)×100%

It was indicated from the above results that all of the attenuated vaccines had very good prophylaxis and treatment effect on the infection caused by the wild-type *V. anguillarum* strains, the % immunoprotection obtained 4 weeks after vaccination by injection was 100%, and the administration safety was very stable within the dose scope ranged from $10^6$-$10^8$CFU/fish.

EXAMPLE 5

Immunoprotection Assay by Immersion, Using *Paralichthys olivaceus* as Test Animal The test fish of *Paralichthys olivaceus* were grouped randomly into 12 groups. Each group had three parallel tanks, 10 fish/tank. The fish were vaccinated by the prepared attenuated live vaccines by immersion. The prepared vaccine stock were diluted with the sterilized aged seawater to $10^6$CFU/ml or $10^8$CFU/ml. The produced solution was added into the empty sterilized tanks to 20 L. Then, each group of test Paralichthys olivaceus were immersed in turn into the solutions to carry out the vaccination by immersion. The immersion time was controlled in a range of 1-15 minutes. No treatment was conducted on the control group. 4 weeks after vaccination, each group of the vaccinated *Paralichthys olivaceus* were artificially challenged by intramuscularly injecting $10^8$ CFU of the wild-type *V. anguillarum* strain per fish. The number of the dead fish were observed and counted within 15 days to calculate the ratio of immunoprotection (see Table 4).

The ratio of immunoprotection was calculated based on the following formula:

% Immunoprotection=(mortality of the control group−mortality of the vaccination group)/(mortality of the control group)×100%

TABLE 3

Immunoprotection assay in which *Paralichthys olivaceus* were challenged 4 weeks after vaccinating with live *V. anguillarum* attenuated vaccines by injection

| Groups | Vaccination Dose | Number of test fish | Number of dead fish | Accumulative Mortality(%) | % Immunoprotection |
|---|---|---|---|---|---|
| MVAV6201 | $10^6$ CFU/fish | 30 | 0 | 0 | 100 |
| MVAV6203 | $10^8$ CFU/fish | 30 | 0 | 0 | 100 |
| MVAV6203 | $10^6$ CFU/fish | 30 | 0 | 0 | 100 |
| MVAV6204 | $10^8$ CFU/fish | 30 | 0 | 0 | 100 |
| MVAV6204 | $10^6$ CFU/fish | 30 | 0 | 0 | 100 |
| Immune Control | saline | 30 | 29 | 96.7 | — |
| Challenge Control | / | 30 | 0 | 0 | — |

Note:
The above data were the average obtained from two batches of independent parallel experiments.

TABLE 4

Immunoprotection assay in which *Paralichthys olivaceus* were challenged 4 weeks after vaccinating with live *V. anguillarum* attenuated vaccines by immersion

| Vaccine type | Vaccination Dose | Number of Test Fish | Number of dead fish | Accumulative Mortality % | % immunoprotection |
|---|---|---|---|---|---|
| MVAV6203 | $10^8$ CFU/ml, 15 min | 30 | 0 | 0 | 100 |
| MVAV6203 | $10^6$ CFU/ml, 15 min | 30 | 0 | 0 | 100 |
| MVAV6204 | $10^8$ CFU/ml, 15 min | 30 | 0 | 0 | 100 |
| MVAV6204 | $10^6$ CFU/ml, 15 min | 30 | 0 | 0 | 100 |
| Control | / | 30 | 30 | 100 | / |
| Control | / | 30 | 0 | 0 | / |

Note:
The above data were the average obtained from two batches of independent parallel experiments It was indicated from the above results that all of the attenuated vaccines had very good prophylaxis and treatment effect on the infection caused by the wild-type *V. anguillarum* strain, the % immunoprotection obtained 4 weeks after vaccination by immersion was 100%, and the administration safety was very stable within the dose scope ranged from $10^6$-$10^8$CFU/fish. The vaccination by immersion produced substantively uniform immune effect as compared with that produced by vaccination by injection, indicating that the vaccine of the invention could be conveniently administered by immersion to produce high efficacy of immunoprotection.

EXAMPLE 6

Cross Immunoprotection Assay against *V. alginolyticus* in which *Epinephelus coioids* were Used as the Test Animal The test fish of *Paralichthys olivaceus* were grouped randomly into 12 groups. Each group had three parallel tanks, 10 fish/tank. The fish were vaccinated by the prepared attenuated live vaccines respectively by immersion and by injection. The vaccination doses by injection were $10^6$CFU/fish and $10^8$CFU/fish, respectively. The vaccine was intraperitoneally administered. The control group was administered with the sterilized saline by injection. The prepared vaccine stock were diluted with the sterilized aged seawater to $10^6$ CFU/ml or $10^8$ CFU/ml. The thus produced solution was added into the empty sterilized tanks to 20 L. Then each group of test *Paralichthys olivaceus* were immersed in turn into the solutions to carry out the vaccination by immersion. The immersion time was controlled in a range of 1-15 minutes. No treatment was conducted on the control group. 4 weeks after vaccination, each group of the vaccinated *Epinephelus coioids* were artificially challenged by intramuscularly injecting $10^8$ CFU of the wild-type *V. alginolyticus* strain per fish. The number of the dead fish were observed and counted within 15 days to calculate the ratio of immunoprotection (see Tables 5 and 6).

TABLE 5

Immunoprotection assay in which *Epinephelus coioids* were challenged 4 weeks after vaccinating with live *V. alginolyticus* attenuated vaccines by immersion

| Vaccine type | Vaccination Dose | Number of test Fish | Number of dead fish | Accumulative Mortality(%) | % Immunoprotection |
|---|---|---|---|---|---|
| MVAV6201 | $10^8$ CFU/ml, 1 min | 30 | 3 | 3.3 | 89.3 |
| MVAV6201 | $10^6$ CFU/ml, 1 min | 30 | 1 | 10 | 96.5 |
| MVAV6203 | $10^8$ CFU/ml, 1 min | 30 | 0 | 0 | 100 |
| MVAV6203 | $10^6$ CFU/ml, 1 min | 30 | 0 | 0 | 100 |
| MVAV6204 | $10^8$ CFU/ml, 1 min | 30 | 0 | 0 | 100 |
| MVAV6204 | $10^6$ CFU/ml, 1 min | 30 | 0 | 0 | 100 |
| Immune Control | / | 30 | 28 | 93.3 | — |
| Challenge Control | / | 30 | 0 | 0 | — |

TABLE 6

Immunoprotection assay in which *Epinephelus coioids* were challenged 4 weeks after vaccinating with live *V. alginolyticus* attenuated vaccines by injection

| Vaccine type | Vaccination Dose | Number of test Fish | Number of dead fish | Accumulative Mortality (%) | % Immunoprotection |
|---|---|---|---|---|---|
| MVAV6201 | $10^8$ CFU/fish | 30 | 1 | 3.3 | 96.5 |
| MVAV6203 | $10^8$ CFU/fish | 30 | 0 | 0 | 100 |
| MVAV6203 | $10^6$ CFU/fish | 30 | 0 | 0 | 100 |
| MVAV6204 | $10^8$ CFU/fish | 30 | 0 | 0 | 100 |
| MVAV6204 | $10^6$ CFU/fish | 30 | 0 | 0 | 100 |
| Immune Control | / | 30 | 28 | 93.3 | / |
| Challenge Control | / | 30 | 0 | 0 | / |

Note:
The above data were the average obtained from two batches of independent parallel experiments The above results showed that all of the attenuated vaccine strains resulted in relatively good immunoprotection for *Epinephelus coioids*, exhibiting good immunogenicity. The results of challenging the *Epinephelus coioids* vaccinated with the attenuated vaccine strains showed very good cross protection. Further, both the vaccination by injection and that by immersion showed uniform immunoprotection efficacy.

Information on Deposition

The deletion mutant strains without marker gene, *Vibrio angullarum* MVAV6201 (pELB1 plasmid is completely deleted), obtained from *Vibrio angullarum* MVM425, was deposited in CCTCC (Wuhan University of China, 430072) on Sep. 19, 2003 with CCTCC accession number of CCTCC-M203069. The other two deletion mutant strains without marker gene, *Vibrio angullarum* MVAV6203 (ΔaroC) and MVAV6204 (ΔaroCΔangE), obtained from *Vibrio angullarum* MVM425, were deposited in CCTCC on Sep. 7 2004 with CCTCC accession numbers of CCTCC-M204066 and CCTCC-M204067, respectively.

We claim:

1. A multivalent attenuated live bacterial vaccine, comprising *V. anguillarum* deletion strain MVAV6203 without marker gene (CCTCC accession number M204066), and/or *V. anguillarum* deletion strain MVAV6204 without marker gene (CCTCC accession number M204067).

2. The multivalent attenuated live bacterial vaccine according to claim 1, wherein the concentration of the *V. anguillarum* deletion strain MVAV6203 without marker gene (CCTCC accession number M204066), and/or *V. anguillarum* deletion strain MVAV6204 without marker gene (CCTCC accession number M204067) is $10^6$-$10^9$ CFU/ml.

3. The multivalent attenuated live bacterial vaccine according to claim 1, which is seawater liquid formulation further comprising marine saline.

4. A method for reducing susceptibility to infection by vibriosis of cultivated fish, comprising injecting or immersing said fish with the multivalent attenuated live bacterial vaccine according to claim 1.

5. The method according to claim 4, wherein the cultivated fish is selected from the group consisting of Percidae, Mugilidae, Balistidae, Bothidae, Pleuronectidae, and Sparidae.

6. The method according to claim 4, wherein said cultivated fish includes *Paralichthys olivaceus*, *Scophthalmus maximus*, *Pagrosomus major*, *Lateolabrax japonicus*, *Epinephelus coioids*, and *Pseudosciaena crocea*.

7. The method according to claim 4, wherein the way of administration includes injection and immersion.

8. The method according to claim 4, wherein the concentration of the administration by injection is $10^4$-$10^8$ CFU/fish.

9. The method according to claim 4, wherein the concentration of the administration by immersion is $10^4$-$10^8$ CFU/ml, and the immersion period is 1-15 minutes.

10. The method according to claim 4, wherein said vibriosis is caused by at least one pathogen selected from the group consisting of *V. anguillarum*, *V. alginoylticus*, *V. parahaemolyticus* and *V harveyi*.

11. The *V. anguillarum* deletion strain MVAV6203 without marker gene with accession number of CCTCC-M204066.

12. The *V. anguillarum* deletion strain MVAV6204 without marker gene with accession number of CCTCC-M204067.

* * * * *